United States Patent [19]
Batts et al.

[11] Patent Number: 6,040,306
[45] Date of Patent: Mar. 21, 2000

[54] METHOD OF TREATING PSORIASIS, ARTHRITIS AND REDUCING THE TOXICITY OF CANCER CHEMOTHERAPY

[75] Inventors: Donald Herman Batts, Kalamazoo, Mich.; Roger G. Ulrich, Gurnee, Ill.

[73] Assignee: Pharmacia & Upjohn Company

[21] Appl. No.: 09/189,466

[22] Filed: Nov. 10, 1998

Related U.S. Application Data

[60] Provisional application No. 60/065,689, Nov. 18, 1997, provisional application No. 60/071,297, Jan. 16, 1998, provisional application No. 60/075,247, Feb. 19, 1998, and provisional application No. 60/077,672, Mar. 12, 1998.

[51] Int. Cl.⁷ .............................. A61P 17/06; A61P 19/02
[52] U.S. Cl. .................. 514/236.8; 514/252; 514/333; 514/340; 514/376
[58] Field of Search .................. 514/236.8, 376

[56] References Cited

U.S. PATENT DOCUMENTS

| | | |
|---|---|---|
| 5,164,510 | 11/1992 | Brickner . |
| 5,231,188 | 7/1993 | Brickner . |
| 5,565,571 | 10/1996 | Barbachyn et al. . |
| 5,652,238 | 7/1997 | Brickner et al. . |
| 5,688,792 | 11/1997 | Barbachyn et al. . |

FOREIGN PATENT DOCUMENTS

| | | |
|---|---|---|
| WO93/09103 | 5/1993 | WIPO . |
| WO93/23384 | 11/1993 | WIPO . |
| WO95/14684 | 6/1995 | WIPO . |

*Primary Examiner*—Robert W. Ramsuer
*Attorney, Agent, or Firm*—Bruce Stein

[57] ABSTRACT

The present invention is a method of treating a person who has psoriasis or arthritis or reducing the toxicity of cancer chemotherapy which comprises administering to the patient an anti-psoriasis effective amount of an oxazolidinone, preferably (S)-N-[[3-[3-fluoro-4-(4-morpholinyl)phenyl]-2-oxo-5-oxazolidinyl]methyl]acetamide.

33 Claims, No Drawings

METHOD OF TREATING PSORIASIS, ARTHRITIS AND REDUCING THE TOXICITY OF CANCER CHEMOTHERAPY

CROSS-REFERENCE TO RELATED APPLICATIONS

This application claims the benefit of US provisional application Ser. Nos. 60/065,689 filed Nov. 18, 1997, 60/071,297 filed Jan. 16, 1998, 60/075,247 filed Feb. 19, 1998 and 60/077,672 filed Mar. 12, 1998 under 35 USC §119(e)(i).

BACKGROUND OF THE INVENTION

1. Field of the Invention

The present invention is the use of known oxazolidinones to treat psoriasis, arthritis and to reduce the toxicity of cancer chemotherapy.

2. Description of the Related Art

U.S. Pat. Nos. 5,164,510, 5,231,188, 5,565,571, 5,652,238 and 5,688,792 all disclose various oxazolidinone antibiotics which are well known to those skilled in the art.

Psoriasis is a well known condition, a proliferative disease of the skin of unknown etiology. It is not known, or believed, to have a microbiologic cause.

Problems experienced by those suffering with psoriasis include intense itching and discomfort, unsightly skin blemishes and chronic scratching resulting in skin infections.

At present there are no cures, only methods of dealing with the clinical symptoms experienced by the patients. These methods of treatment include avoiding drying of the skin and irritation of skin, use of topical steroid cremes and ointments, use of crude coal tar (1–5% in an ointment base) applied topically, ultraviolet light therapy, topical vitamin D (calcipitriol), oral methotrexate for severe cases (a drawback to this therapy is that methotrexate causes severe liver damage if not careful), use of etretrinate (a synthetic retinoid) for severe cases (however a drawback to this therapy is that it is associated with severe deformities in fetuses if a female patient is pregnant).

There is no cure for psoriasis, but rather treatments which may induce a remission for a period of time. Since the pathogenesis of psoriasis is unknown, the reason why the various treatments do not fully succeed is not known but it is likely that present treatments are not treating the root cause of psoriasis.

While there are number of pharmaceutical agents available for treating psoriasis, none treat the condition/disease as well as psoriasis sufferers or physicians would like.

Arthritis, inflammation of the joint tissues, has numerous causes including bacterial infection (septic arthritis), degeneration of articular surfaces (osteoarthritis), immunologic reaction against joint tissues (rheumatoid arthritis), crystal induced arthritis (gouty arthritis, pseudogout) and other miscellaneous causes (Reiter's syndrome, etc). One common thread in all of these is inflammation in and around the joint. Present day therapeutics for arthritis are not curative unless the arthritis is infectious and the underlying pathogen is eliminated by an antibiotic. For other types of arthritis medications can reduce pain or inflammation but do not cure the disease. The OXAZOLIDINONEs can be used to treat the inflammation and pain caused by arthritis, including those types of arthritis which are not caused by infection. This is important since all of the medications presently available to treat arthritis have severe side effects. Steroidal medications (glucocorticoids like prednisone and cortisol) give stomach ulcers, cataracts, reduced resistance to infection, weight gain and thinning of skin. Non-steroidal anti-inflammatory drugs (NSAIDS such as indomethacin or ibuprofen among others) can cause stomach ulcers, reduced kidney function and bone marrow effects. Chemotherapeutic agents (like methotrexate) can have severe adverse effects on bone marrow and liver function. The OXAZOLIDINO-NEs provide the opportunity for relief of symptoms of inflammation for patients intolerant of other types of arthritis medications.

Patients who have cancer and need to undergo anti-cancer chemotherapy have the problem that the dose limiting factor in their treatment is the suppression of bone marrow. The present invention prevents and reduces the amount of suppression of bone marrow and injury to intestinal crypt cells (the cells that produce new intestinal cells). By preventing damage to the hematopoietic cells in general and the bone marrow cells in particular, physicians can prevent or reduce the toxicity of the chemotherapeutic agents and therefore can treat cancer patients longer and/or with higher doses and with reduced risks of complications. All this means a more successful outcome for the patient.

At present there is no product on the market that prevents damage to hematopoietic and/or intestinal cells from exposure to anti-cancer chemotherapeutic agents. There are products which are given after anti-cancer chemotherapy to try and help the patient recover, but this is not the same as the preventive method of the present invention. These agents include bone marrow colony stimulating factors such as GM-CSF. There are protective agents known, but not in clinical use, for dealing with radiation therapy such as glutathione derivatives, but these do not prevent the problems associated with anti-cancer chemotherapy.

SUMMARY OF INVENTION

Disclosed is a method of treating a person who has psoriasis which comprises administering to the patient an anti-psoriasis effective amount of an oxazolidinone selected from the group consisting of:

(S)-N-[[3-[3-fluoro-4-[4-(hydroxyacetyl)-1-piperazinyl]-phenyl]-2-oxo-5-oxazolidinyl]methyl]acetamide, (S)-N-[[3-[3-fluoro-4-(4-morpholinyl)phenyl]-2-oxo-5-oxazolidinyl]methyl]acetamide,

[4(S)-cis]-(-)-N-[[3-[3-Fluoro-4-(tetrahydro-1-oxido-2H-thiopyran-4-yl)phenyl]-2-oxo-5-oxazolidinyl]methyl]acetamide, N-((5S)-3-(3-fluoro-4-(4-(2-fluoroethyl)-3-oxopiperazin-1-yl)phenyl)-2-oxooxazolidin-5-ylmethyl)acetamide, (S)-N-[[3-[5-(3-pyridyl)thiophen-2-yl]-2-oxo-5-oxazolidinyl]methyl]acetamide and (S)-N-[[3-[5-(4-pyridyl)pyrid-2-yl]-2-oxo-5-oxazolidinyl]methyl]acetamide and pharmaceutically acceptable salts thereof.

Also disclosed is a method of treating a person who has arthritis which comprises administering to the patient an anti-arthritis effective amount of an oxazolidinone selected from the group consisting of the six oxazolidinones set forth above.

Further disclosed is a method of reducing damage to hematopoietic cells and intestinal cells in a person being treated with one or more anti-cancer chemotherapeutic agents which comprises administering to the human an anti-cytotoxic effective amount of an oxazolidinone selected from the group consisting of the sxi oxazolidinones set forth above.

DETAILED DESCRIPTION OF THE INVENTION

The oxazolidinones of the present invention are known, see EXAMPLES 1 thru 6 (OXAZOLIDINONEs) and pharmaceutically acceptable salts thereof Suitable pharmaceutical acceptable salts include the acid addition salts from the both inorganic and organic acids including hydrochloric, hydrobromic, sulfuric, phosphoric, sulfonic acids, methanesulfonic, gluconic, galacturonic, citric, oxylatic and acetic.

It is preferred that the person being treated for psoriasis or arthritis or with cancer chemotherapy agents with OXAZOLIDINONEs does not have a gram positive bacterial infection at the time of being treated.

In treating psoriasis, the OXAZOLIDINONEs can either be used individually or in combination with each other or in combination with non-OXAZOLIDINONEs.

In treating psoriasis, the OXAZOLIDINONEs are administered orally, parenterally (IV), topically or rectally.

When administered orally, the OXAZOLIDINONEs can be administered in tablet, capsule or liquid (suspension, syrup or solution) dosage form. Regardless of the dosage form, an anti-psoriasis effective amount of the OXAZOLIDINONEs is from about 50 mg to about 1,200 mg/day. It is preferred that the OXAZOLIDINONEs be given in two or more divided doses, more preferably in two divided doses.

When administered parenterally, the OXAZOLIDINONEs should be administered IV. The IV infusion should be adjusted such that the flow rate delivers an anti-psoriasis effective amount of from about 50 mg to about 1,200 mg/day. (S)-N-[[3-[3-Fluoro-4-(4-morpholinyl)phenyl]-2-oxo-5-oxazolidinyl]methyl]acetamide is virtually 100% bioavailable. Therefore, the patient will achieve approximately the same blood levels with the same dose regardless of whether it is given orally of parenterally.

When applied topically, the OXAZOLIDINONEs can be applied in many different pharmaceutical dosage forms all well known to those skilled in the art. These include as a solution, cream, ointment, gel, lotion, suspension or emulsion, etc. Regardless of the topical pharmaceutical dosage form selected, the concentration of the OXAZOLIDINONEs should be from about 0.01% to about 10% (wt/wt). Regardless of the pharmaceutical dosage form, the topical formulation should be applied one to four times daily.

When administered rectally, the OXAZOLIDINONEs should be administered as a suppository which delivers an anti-psoriasis effective amount of from about 50 mg to about 1,200 mg/day.

When administered systemically, whether orally, parenterally or rectally the OXAZOLIDINONEs should be administered either continuously or in cyclic courses of 7–28 days every 1 to 12 months. When administered topically, the OXAZOLIDINONEs should be applied either daily for 7 to 28 days every 1–12 months.

In treating arthritis, the OXAZOLIDINONEs can either be used individually or in combination with each other or in combination with non-OXAZOLIDINONEs.

In treating arthritis, the OXAZOLIDINONEs are administered orally, parenterally (IV), topically or rectally.

When administered orally, the OXAZOLIDINONEs can be administered in tablet, capsule or liquid (suspension, syrup or solution) dosage form. Regardless of the dosage form, an anti-arthritis effective amount of the OXAZOLIDINONEs is from about 50 mg to about 1,200 mg/day. It is preferred that the OXAZOLIDINONEs be given in two or more divided doses, more preferably in two divided doses.

When administered parenterally, the OXAZOLIDINONEs should be administered IV. The IV infusion should be adjusted such that the flow rate delivers an anti-arthritis effective amount of from about 50 mg to about 1,200 mg/day. This can be done by a continuous infusion, or as divided doses given as short term infusions of 30–90 minutes, preferably twice a day.

When applied topically, the OXAZOLIDINONEs can be applied in many different pharmaceutical dosage forms all well known to those skilled in the art. These include a solution, cream, ointment, gel, lotion, suspension or emulsion. Regardless of the pharmaceutical dosage form selected, the concentration of the OXAZOLIDINONEs should be from about 0.01% to about 10% (wt/wt). Regardless of the pharmaceutical dosage form, the topical formulation should be applied one to four times daily.

When administered rectally, the OXAZOLIDINONEs should be administered as a suppository which delivers an anti-arthritis effective amount of from about 50 mg to about 1,200 mg/day.

When administered systemically, whether orally, parenterally or rectally the OXAZOLIDINONEs should be administered either continuously or in cyclic courses of 7–28 days every 1 to 12 months. When administered topically, the OXAZOLIDINONEs should be applied either daily for 7 to 28 days every 1–12 months.

The exact dosage and frequency of administration depends on the particular OXAZOLIDINONE used, the severity of the condition being treated, the age, weight, general physical condition of the particular patient, other medication the individual may be taking as is well known to those skilled in the art and can be more accurately determined by measuring the blood level or concentration of the OXAZOLIDINONE in the patient's blood and/or the patient's response to the particular condition being treated.

Individuals who have cancer and are treated with anti-cancer chemotherapeutic agents experience damage to their hematopoietic and intestinal cells. There are three types of hematopoietic cells. These are bone marrow cells, spleen cells and liver cells. It is preferred that the hematopoietic cells be bone marrow cells. The present method also prevents/reduces damage to intestinal crypt cells. These are the cells located in the intestinal area that produce new intestinal cells.

By preventing damage to the hematopoietic cells in general and the bone marrow cells in particular, physicians can prevent or reduce the toxicity of the chemotherapeutic agents and therefore can treat cancer patients longer and/or with higher doses and with reduced risks of complications. All this means a more successful outcome for the patient.

In preventing/reducing the damage to hematopoietic cells and intestinal cells from exposure to anti-cancer chemotherapeutic agents, the OXAZOLIDINONEs can either be used individually or in combination with each other or in combination with non-OXAZOLIDINONEs.

In some cases the present method will prevent the damage from occurring and in other cases it will reduce the damage that would have occurred if the patient had not been treated with the OXAZOLIDINONEs. As used here, reduction is a form of prevention; prevention is the ultimate reduction.

The present method is practiced by preferably pre-treating the patient for about 2 to about 20 days prior to the patient being treated with an anti-cancer chemotherapeutic agent. It is more preferable that the pretreatment be from about 5 to about 7 days prior to the patient being treated with an anti-cancer chemotherapeutic agent. Alternatively, the OXAZOLIDINONEs can be administered concurrently with the anti-cancer chemotherapeutic agent.

Anti-cancer chemotherapeutic agents which are included in the method of reducing damage according to the present invention are selected from four different types of chemotherapeutic agents. These are:

(1) DNA-interactive agents (including alkylating agents, DNA strand-breakage agents, DNA topoisomerase I and II inhibitors, DNA minor groove binders) such as chlorambucil, cyclophosphamide, thiotepa, busulfan, carmustine, cisplatin, carboplatin, mitomycin, procarbazine, bleomycin, amsacrine, daunorubicin, doxorubicin, etoposide, plicamycin, campothecin and ironotecan;

(2) antimetabolites (including folate antagonists, purine antagonists, pyrimidine antagonists) such as methotrexate, mercaptopurine, eloxuridine and fluorouracil;

(3) tubulin-interactive agents such as vinblastine, vincristine and paclitaxel;

(4) hormonal agents such as dienestrol, diethylstilbestrol, estradiol, tamoxifon and fluoxymesterone.

It is preferred that the anti-cancer chemotherapeutic agent be selected from the group consisting of chlorambucil, cyclophosphamide, thiotepa, busulfam, carmustine, cisplatin, carboplatin, mitomycin, procarbazine, bleomycin, amsacrine, daunorubicin, doxorubicin, etoposide, plicamycin, camptothecin, ironotecan, methotrexate, mercaptopurine, eloxuridine, fluorouracil, vinblastin, vincristine, paclitaxel, dienestrol, diethylstilbestrol, estradiol, tamoxifon and fluoxymesterone. It is more preferred that the anti-cancer chemotherapeutic agent be selected from the group consisting of etoposide, irinotecan, fluorouricil and paclitaxel.

In preventing/reducing the damage to hematopoietic cells and intestinal cells from exposure to anti-cancer chemotherapeutic agents, the OXAZOLIDINONEs are administered orally, parenterally (IV) or rectally. It is preferred that the OXAZOLIDINONEs be administered orally or by IV, more preferably orally.

When administered orally, the OXAZOLIDINONEs can be administered in solid (tablet or capsule) or liquid (suspension, syrup or solution) dosage form. Regardless of the dosage form, a cytostatic or an anti-cytotoxic effective amount of the OXAZOLIDINONEs is from about 50 mg to about 1,200 mg/day. It is preferred that the OXAZOLIDINONEs be given in two or more divided doses, more preferably in two divided doses.

When administered parenterally, the OXAZOLIDINONEs should be administered IV. The IV infusion should be adjusted such that the flow rate delivers an anti-cytotoxic effective amount of from about 50 mg to about 1,200 mg/day. This can be done by a continuous infusion, or as divided doses given as short term infusions of 30–90 minutes, preferably twice a day.

When administered rectally, the OXAZOLIDINONEs should be administered as a suppository which delivers an anti-cytotoxic effective amount of from about 50 mg to about 1,200 mg/day.

When administered systemically, whether orally, parenterally or rectally the OXAZOLIDINONEs should be administered either continuously or in cyclic courses of 7–28 days every 1 to 12 months.

The exact dosage and frequency of administration depends on the particular OXAZOLIDINONE used, the particular anti-cancer chemotherapeutic agent used, the dose of the anti-cancer chemotherapeutic agent, the severity of the condition being treated, the age, weight, general physical condition of the particular patient, other medication the individual may be taking as is well known to those skilled in the art and can be more accurately determined by measuring the blood level or concentration of the OXAZOLIDINONE in the patient's blood and/or the patient's response to the particular condition being treated.

DEFINITIONS AND CONVENTIONS

The definitions and explanations below are for the terms as used throughout this entire document including both the specification and the claims.

DEFINITIONS

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When the solubility of a solid in a solvent is used the ratio of the solid to the solvent is weight/volume (wt/v).

When the % active ingredient of a pharmaceutical formulation is set forth, it is the ratio of the active ingredient of the entire pharmaceutical formulation and is expressed as weight/weight (wt/wt).

Alcohol refers to ethyl alcohol.

IV refers to parenteral administration by the intravenous route.

OXAZOLIDINONES refers to the compounds of EXAMPLES 1 thru 6.

Anti-cytotoxic refers to reducing and/or preventing normal cell death.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

(S)-N-[[3-[3-Fluoro-4-[4-(hydroxyacetyl)-1-piperazinyl]-phenyl]-2-oxo-5-oxazolidinyl]methyl]acetamide (S)-N-[[3-[3-Fluoro-4-[4-(hydroxyacetyl)-1-piperazinyl]-phenyl]-2-oxo-5-oxazolidinyl]methyl]acetamide is known, see U.S. Pat. No. 5,652,238, EXAMPLE 1.

EXAMPLE 2

(S)-N-[[3-[3-Fluoro-4-(4-morpholinyl)phenyl]-2-oxo-5-oxazolidinyl]methyl]acetamide (S)-N-[[3-[3-Fluoro-4-(4-morpholinyl)phenyl]-2-oxo-5-oxazolidinyl]methyl]acetamide is known, see U.S. Pat. No. 5,688,792, EXAMPLE 5.

EXAMPLE 3

[4(S)-cis]-(−)-N-[[3-[3-Fluoro-4-(tetrahydro-1-oxido-2H-thiopyran-4-yl) phenyl]-2-oxo-5-oxazolidinyl]methyl] acetamide A mixture of (S)-(−)-N-[[3-[3-fluoro-4-(3,6-dihydro-2H-thiopyran-4-yl)phenyl]-2-oxo-5-oxazolidinyl]methyl] acetamide S-oxide (International Publication No. WO 97/09328, 4.50 g) and platinum oxide (697 mg) in methanol (164 ml) is shaken on the Parr apparatus under a hydrogen atmosphere at 40 psi for 18 hours. The catalyst is then removed by filtration through Celite, and the filtrate is concentrated under reduced pressure and the residue chromatographed on silica gel (230–400 mesh, 350 g), eluting with a gradient of methanol/methylene chloride (3/97–7/93). The appropriate fractions (those fractions with an $R_f$=0.44 by TLC; methanol/chloroform, 10/90) are pooled and concentrated to give the title compound, mp 203–204°.

EXAMPLE 4

N-((5S)-3-(3-Fluoro-4-(4-(2-fluoroethyl)-3-oxopiperazin-1-yl) phenyl)-2-oxooxazolidin-5-ylmethyl)acetamide N-((5S)-3-(3Fluoro-4-(4-(2-fluoroethyl)-3-oxopiperazin-1-yl)phenyl)-2-oxooxazolidin-5-ylmethyl)acetamide is known, see International Publication WO97/27188 (Example 4).

1-t-Butoxycarbonyl-3-oxopiperazine (21.6 g) is dissolved in dry DMF (500 ml) and potassium t-butoxide (24.2 g) is added. The mixture is stirred at 20–25° for 30 minutes, then 1-(4-methylphenylsulfonyloxy)-2-fluoroethane (J. Med. Chem., 23(9), 985–90 (1980), 25.9 g) is added and stirring continued at the same temperature for 24 hours. The solvent is removed and the residue partitioned between ethyl acetate and water. The organic phase is washed with water and concentrated. The residue is dissolved in isopropanol and diluted with iso-hexane forming a precipitate which is removed by filtration. The mixture is chromatographed (silica; eluting with a gradient increasing in polarity from 0 to 50% isopropanol in iso-hexane) to give 1-t-butoxycarbonyl-4-(2-fluoroethyl)-3-oxopiperazine.

1-t-Butoxycarbonyl-4-(2-fluoroethyl)-3-oxopiperazine (6.65 g) is dissolved in dichloromethane (500 ml), cooled in an ice-bath and trifluoroacetic acid (150 ml) added. The mixture is stirred at the same temperature for 2 hours. The solvent is removed to give a crude product which is dissolved in the minimum volume of ethyl acetate. Slow addition of ether causes precipitation of 1-(2-fluoroethyl)-2-oxopiperazine as the mono trifluoroacetic acid salt.

1-(2-Fluoroethyl)-2-oxopiperazine trifluoroacetate (6.1 g) is dissolved in acetonitrile (100 ml). N,N-Diisopropylethylamine (13 ml) is added to the mixture, followed by 3,4-difluoronitrobenzene (3.39 g) and the mixture heated to reflux for 18 hours. The solvent is removed and the residue chromatographed (silica; eluting with a gradient increasing in polarity from 0 to 4% methanol in dichloromethane) to give 3-fluoro-4-(4-{2-fluoroethyl}-3-oxopiperazin-1-yl)nitrobenzene.

3-Fluoro-4-(4-{2-fluoroethyl}-3-oxopiperazin-1-yl) nitrobenzene (4.35 g) is dissolved in a mixture of ethyl acetate (250 ml) and DMF (5 ml), and the solution flushed with argon. Palladium (10% on carbon, 200 mg) is added and the mixture hydrogenated under ambient pressure. After gas uptake had ceased, the mixture is filtered through celite and solvent removed. The residue is taken up in ethyl acetate, washed twice with water, dried over magnesium sulfate and the solvent is removed to give 5-amino-2-[4-(2-fluoroethyl)-3-oxopiperazin-1-yl]fluorobenzene which is used without further purification.

5-Amino-2-(4-[2-fluoroethyl]-3-oxopiperazin-1-yl) fluorobenzene (2.6 g) is dissolved in dry dichloromethane (50 ml) under argon. Pyridine (1.03 ml) is added, and the mixture cooled to −20°. Benzyl chloroformate (1.6 ml) is added and the mixture stirred for 10 minutes at −20°, before allowing the temperature to rise to 20–25° over 1.5 hours. The solvents are removed and the residue is dissolved in dichloromethane and washed with sodium bicarbonate solution. After drying over magnesium sulfate and removal of the solvent, the residue is chromatographed (silica, eluting with a gradient increasing in polarity from 0 to 5% methanol in dichloromethane) to give 5-benzyloxycarbonylamino-2-(4-[2-fluoroethyl]-3-oxopiperazin-1-yl)fluorobenzene.

A solution of lithium t-butoxide is prepared by addition of n-butyllithium (1.6 M in hexane, 2.9 ml) to a stirred solution of t-butanol (0.43 g) in anhydrous THF (10 ml) at −10° under argon. After cooling to −70°, a solution of 5-benzyloxycarbonylamino-2-(4-[2-fluoroethyl]-3-oxopiperazin-1-yl)fluorobenzene (1.5 g) in dry THF (15 ml) is added. After 10 minutes, (R)-glycidylbutyrate (0.67 g) in dry THF (15 ml) is added to the resulting mixture, and stirring continued at −70° for 15 minutes, before allowing the temperature to rise to 20–250 over 16 hours. Methanol (10 ml) is added, followed by saturated sodium bicarbonate solution (20 ml) and water (10 ml). The organic phase is separated and extracted into ethyl acetate (3×25 ml), washed with saline and dried over magnesium sulfate. The solvent is removed and the residue purified by chromatography (silica; eluting with a gradient increasing in polarity from 0 to 3% methanol in dichloromethane) to give (5R)-3-(3-fluoro-4-[4-(2-fluoroethyl)-3-oxopiperazin-1-yl]phenyl)-5-hydroxymethyloxazolidin-2-one.

(5R)-3-(3-Fluoro-4-[4-(2-fluoroethyl)-3-oxopiperazin-1-yl]phenyl)-5-hydroxymethyloxazolidin-2-one (0.8 g) is dissolved in pyridine (15 ml) and the mixture cooled to 0°. Triethylamine (0.38 ml) and methanesulfonyl chloride (0.19 ml) are added to the mixture, and stirring continued at 20–25° for 2 hours. The solvent is removed and the residue dissolved in dichloromethane, washed with water, saline, dried over magnesium sulfate and concentrated. The resulting residue is triturated with ether to give (5R)-3-(3-fluoro-4-[4-(2-fluoroethyl)-3-oxopiperazin-1-yl]phenyl)-5-(methanesulfonyloxymethyl)oxazolidin-2-one (0.76 g) which is used without further purification.

(5R)-3-(3-Fluoro-4-[4-(2-fluoroethyl)-3-oxopiperazin-1-yl]-5-(methanesulfonyloxymethyl)oxazolidin-2-one (719 mg) is dissolved in dry DMF (15 ml) and sodium azide (647 mg) is added to the mixture. The mixture is heated at 80° for 6 hrs and then concentrated to dryness. The resulting residue is dissolved in ethyl acetate, washed twice with water, and dried over magnesium sulfate. Removal of the solvent gives (5R)-5-azidomethyl-3-(3-fluoro-4-(4-(2-fluoroethyl)-3-oxopiperazin-1-yl)phenyl)oxazolidin-2-one (413 mg) which is used without further purification.

(5R)-5-Azidomethyl-3-(3-fluoro-4-[4-(2-fluoroethyl)-3-oxopiperazin-1-yl]phenyl)oxazolidin-2-one (360 mg) is dissolved in dry DMF (20 ml) and the mixture purged with argon. Palladium (10% on carbon, 72 mg) is added, followed by acetic anhydride (0.17 ml) and the mixture stirred at 20–25° under hydrogen confined in a balloon for 3 hr. The mixture is filtered through celite, concentrated to dryness and partitioned between ethyl acetate and water. The organic extract is washed with saline, dried over magnesium sulfate and concentrated. The residue is chromatographed (silica gel; eluting with a gradient increasing in polarity from 0 to 2.5% methanol/dichloromethane). The appropriate fractions are pooled and concentrated to give the title compound.

EXAMPLE 5

(S)-N-[[3-[5-(3-Pyridyl)thiophen-2-yl]-2-oxo-5-oxazolidinyl]methyl]acetamide (S)-N-[[3-[5-(3-Pdyl)thiophen-2-yl]-2-oxo-5-oxazolidinyl]methyl]acetamide is known, see U.S. Pat. No. 5,698,574 (Example 124).

EXAMPLE 6

(S)-N-[[3-[5-(4-Pyridyl)pyrid-2-yl]-2-oxo-5-oxazolidinyl] methyl]acetamide hydrochloride (S)-N-[[3-[5-(4-Pyridyl)pyrid-2-yl]-2-oxo-5-oxazolidinyl]methyl]acetamide hydrochloride is prepared following the general procedure of U.S. Pat. No. 5,627,181 EXAMPLEs 36 and 52 and making non-critical variations but using a 4-pyridinyl adduct.

EXAMPLE A
47 Year Old White Male—Psoriasis

A 47 year old white male had a history of psoriasis since age 32. He had chronic psoriatic lesions of both elbows, groin, left leg, right leg, and lower back. The lesions were treated in the past with coal tar and topical steroids but not UV light. He was allergic to the excipients in the steroidal topical preparations.

He was treated with 625 mg of (S)-N-[[3-[3-fluoro-4-(4-morpholhnyl)phenyl]-2-oxo-5-oxazolidinyl]methyl] acetamide IV twice daily for five days and then with 625 mg of the same pharmaceutical orally twice daily for nine days. Hence, the patient was given 625 mg of (S)-N-[[3-[3-fluoro-4-(4-morpholinyl)phenyl]-2-oxo-5-oxazolidinyl]methyl] acetamide twice daily for fourteen days and noticed an immediate improvement in his psoriasis as soon as he started taking the medication. He had a complete clearing of the psoriasis from the time he took the medication until three months later when it gradually began to return. After six months it had returned to the pretreatment state. During the time he took the oxazolidinone he did not use any other psoriasis treatment.

EXAMPLE B
50 Year Old White Male—Arthritis

A 50 year old white male (Subject No 1912) who had a history of chronic obstructive pulmonary disease (i.e. he was a smoker), hypertension, coronary artery disease and arthritis of the "legs, arms and shoulders" for which he took non steroidal antiinflammatory agents including aspirin, developed community acquired pneumonia with *Streptococcus pneumoniae* as evidenced by an abnormal chest X-ray. He is treated with 625 mg of (S)-N-[[3-[3-fluoro-4-(4-morpholinyl)phenyl]-2-oxo-5-oxazolidinyl]methyl] acetamide twice daily intravenously for 3 days followed by 8 days of oral (S)-N-[[3-[3-fluoro-4-(4-morpholinyl) phenyl]-2-oxo-5-oxazolidinyl]methyl]acetamide at the same dose.

At long term follow up the patient stated that his arthritis was gone and he was taking no medications.

CHART A

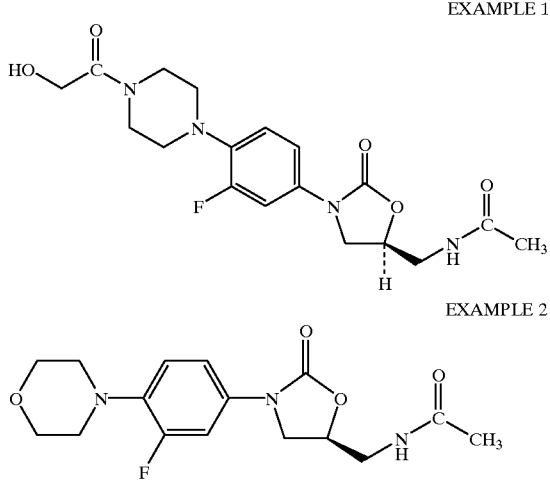

EXAMPLE 1

EXAMPLE 2

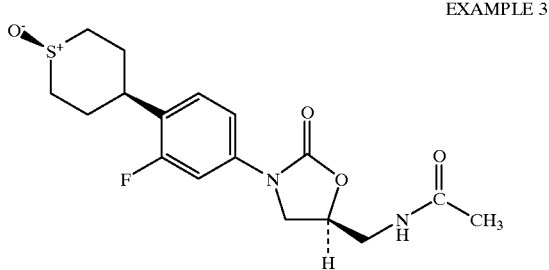

EXAMPLE 3

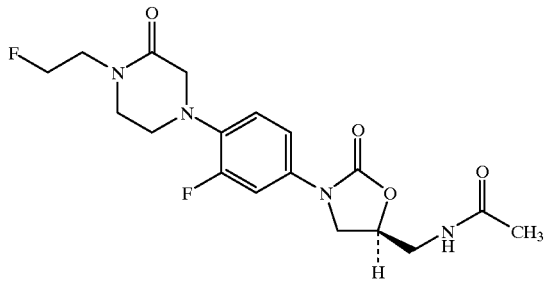

EXAMPLE 4

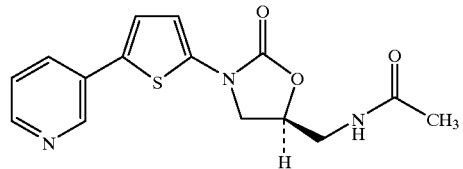

EXAMPLE 5

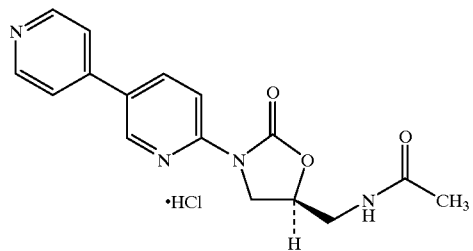

EXAMPLE 6

We claim:
1. A method of treating a person who has psoriasis which comprises administering to the patient an anti-psoriasis effective amount of an oxazolidinone selected from the group consisting of
   (S)-N-[[3-[3-fluoro-4-[4-(hydroxyacetyl)-1-piperazinyl]-phenyl]-2-oxo-5-oxazolidinyl]methyl]acetamide,
   (S)-N-[[3-[3-fluoro-4-(4-morpholinyl)phenyl]-2-oxo-5-oxazolidinyl]methyl]acetamide,
   [4(S)-cis]-(−)-N-[[3-[3-Fluoro-4-(tetrahydro-1-oxido-2H-thiopyran-4-yl) phenyl]-2-oxo-5-oxazolidinyl] methyl]acetamide,
   N-((5S)-3-(3-fluoro-4-(4-(2-fluoroethyl)-3-oxopiperazin-1-yl)phenyl)-2-oxooxazolidin-5-ylmethyl)acetamide,
   (S)-N-[[3-[5-(3-pyridyl)thiophen-2-yl]-2-oxo-5-oxazohdinyl]methyl]acetamide and
   (S)-N-[[3-[5-(4-pyridyl)pyrid-2-yl]-2-oxo-5-oxazolidinyl]methyl]acetamide and pharmaceutically acceptable salts thereof.
2. A method of treating a person who has psoriasis according to claim 1 and who does not have a gram positive bacterial infection.
3. A method of treating a person who has psoriasis according to claim 1 where the anti-psoriasis effective amount is administered orally.

4. A method of treating a person who has psoriasis according to claim 3 where the anti-psoriasis effective amount is from about 50 to about 1,200 mg/day.

5. A method of treating a person who has psoriasis according to claim 1 where the anti-psoriasis effective amount is administered topically as a solution, cream, ointment, gel, lotion, suspension or emulsion.

6. A method of treating a person who has psoriasis according to claim 5 where the anti-psoriasis effective amount is from about 0.01% to about 10%.

7. A method of treating a person who has psoriasis according to claim 1 where the anti-psoriasis effective amount is administered IV.

8. A method of treating a person who has psoriasis according to claim 7 where the anti-psoriasis effective amount is from about 50 to about 1,200 mg/day.

9. A method of treating a person who has psoriasis according to claim 1 where the anti-psoriasis effective amount is administered rectally.

10. A method of treating a person who has psoriasis according to claim 9 where the anti-psoriasis effective amount is from about 50 to about 1,200 mg/day.

11. A method of treating a person who has psoriasis according to claim 1 where the oxazolidinone is (S)-N-[[3-[3-fluoro-4-(4-morpholinyl)phenyl]-2-oxo-5-oxazolidinyl]methyl]acetamide.

12. A method of treating a person who has arthritis which comprises administering to the patient an anti-arthritis effective amount of an oxazolidinone selected from the group consisting of (S)-N-[[3-[3-fluoro-4-[4-(hydroxyacetyl)-1-piperazinyl]-phenyl]-2-oxo-5-oxazolidinyl]methyl]acetamide, (S)-N-[[3-[3-fluoro-4-(4-morpholinyl)phenyl]-2-oxo-5-oxazolidinyl]methyl]acetamide,

[4(S)-cis]-(-)-N-[[3-[3-Fluoro-4-(tetrahydro-1-oxido-2H-thiopyran-4-yl) phenyl]-2-oxo-5-oxazolidinyl]methyl]acetamide, N-((5S)-3-(3-fluoro-4-(4-(2-fluoroethyl)-3-oxopiperazin-1-yl)phenyl)-2-oxooxazolidin-5-ylmethyl)acetamide, (S)-N-[[3-[5-(3-pyridyl)thiophen-2-yl]-2-oxo-5-oxazolidinyl]methyl]acetamide and (S)-N-[[3-[5-(4-pyridyl)pyrid-2-yl]-2-oxo-5-oxazolidinyl]methyl]acetamide and pharmaceutically acceptable salts thereof.

13. A method of treating a person who has arthritis according to claim 12 and who does not have a gram positive bacterial infection.

14. A method of treating a person who has arthritis according to claim 12 where the anti-arthritis effective amount is administered orally.

15. A method of treating a person who has arthritis according to claim 14 where the anti-arthritis effective amount is from about 50 to about 1,200 mg/day.

16. A method of treating a person who has arthritis according to claim 12 where the anti-arthritis effective amount is administered topically as a solution, cream, ointment, gel, lotion, suspension or emulsion.

17. A method of treating a person who has arthritis according to claim 16 where the anti-arthritis effective amount is from about 0.01% to about 10%.

18. A method of treating a person who has arthritis according to claim 1 where the anti-arthritis effective amount is administered IV.

19. A method of treating a person who has arthritis according to claim 18 where the anti-arthritis effective amount is from about 50 to about 1,200 mg/day.

20. A method of treating a person who has arthritis according to claim 12 where the anti-arthritis effective amount is administered rectally.

21. A method of treating a person who has arthritis according to claim 20 where the anti-arthritis effective amount is from about 50 to about 1,200 mg/day.

22. A method of treating a person who has arthritis according to claim 12 where the oxazolidinone is (S)-N-[[3-[3-fluoro-4-(4-morpholinyl)phenyl]-2-oxo-5-oxazolidinyl]methyl]acetamide.

23. A method of reducing damage to hematopoietic cells and intestinal cells in a person being treated with one or more anti-cancer chemotherapeutic agents which comprises administering to the human an anti-cytotoxic effective amount of an oxazolidinone selected from the group consisting of:

(S)-N-[[3-[3-fluoro-4-[4-(hydroxyacetyl)-1-piperazinyl]-phenyl]-2-oxo-5-oxazolidinyl]methyl]acetamide, (S)-N-[[3-[3-fluoro-4-(4-morpholinyl)phenyl]-2-oxo-5-oxazolidinyl]methyl]acetamide,

[4(S)-cis]-(-)-N-[[3-[3-Fluoro-4-(tetrahydro-1-oxido-2H-thiopyran-4-yl) phenyl]-2-oxo-5-oxazolidinyl]methyl]acetamide, N-((5S)-3-(3-fluoro-4-(4-(2-fluoroethyl)-3-oxopiperazin-1-yl)phenyl)- 2-oxooxazolidin-5-ylmethyl)acetamide, (S)-N-[[3-[5-(3-pyridyl)thiophen-2-yl]-2-oxo-5-oxazolidinyl]methyl]acetamide and (S)-N-[[3-[5-(4-pyridyl)pyrid-2-yl]-2-oxo-5-oxazolidinyl]methyl]acetamide and pharmaceutically acceptable salts thereof.

24. A method of reducing damage according to claim 23 where the human does not have a gram positive bacterial infection.

25. A method of reducing damage according to claim 23 where the hematopoietic cell is a bone marrow cell.

26. A method of reducing damage according to claim 23 where the hematopoietic cell is a spleen cell.

27. A method of reducing damage according to claim 23 where the human is pretreated with the oxazolidinone for a period of from about 2 to about 20 days prior to treatment with an anti-cancer chemotherapeutic agent.

28. A method of reducing damage according to claim 27 where the pretreatment period is from about 5 to about 7 days.

29. A method of reducing damage according to claim 23 where the oxazolidinone is administered concurrently with the anti-cancer chemotherapeutic agent.

30. A method of reducing damage according to claim 23 where the anti-cancer chemotherapeutic agent is selected from the group consisting of:

chlorambucil, cyclophosphamide, thiotepa, busulfam, carmustine, cisplatin, carboplatin, mitomycin, procarbazine, bleomycin, amsacrine, daunorubicin, doxorubicin, etoposide, plicamycin, camptothecin, ironotecan, methotrexate, mercaptopurine, eloxuridine, fluorouracil, vinblastin, vincristine, paclitaxel, dienestrol, diethylstilbestrol, estradiol, tamoxifon and fluoxymesterone.

31. A method of reducing damage according to claim 30 where the anti-cancer chemotherapeutic agent is selected from the group consisting of etoposide, irinotecan, fluorouricil and paclitaxel.

32. A method of reducing damage according to claim 23 where the anti-cytotoxic effective amount of the oxazolidinone is from about 50 mg to about 1,200 mg/day.

33. A method of reducing damage according to claim 23 where the oxazolidinone is (S)-N-[[3-[3-fluoro-4-(4-morpholinyl)phenyl]-2-oxo-5-oxazolidinyl]methyl]acetamide.

* * * * *